United States Patent [19]
Walulik

[11] Patent Number: 5,997,537
[45] Date of Patent: Dec. 7, 1999

[54] RING SYSTEM FOR EXTERNAL FIXATION OF BONE AND RELATED METHOD

[75] Inventor: Stephen B. Walulik, Phillipsburg, N.J.

[73] Assignee: Electro Biology, Inc., Parsippany, N.J.

[21] Appl. No.: 09/086,256

[22] Filed: May 28, 1998

[51] Int. Cl.[6] .................................................. A61B 17/62
[52] U.S. Cl. ............................................. 606/56; 606/59
[58] Field of Search ............................... 606/54, 55, 56, 606/57, 58, 59

[56] References Cited

U.S. PATENT DOCUMENTS

| | | |
|---|---|---|
| D. 367,529 | 2/1996 | Price et al. . |
| D. 367,531 | 2/1996 | Price et al. . |
| 4,127,119 | 11/1978 | Kronner . |
| 4,535,763 | 8/1985 | Jaquet ........................................ 606/56 |
| 4,784,125 | 11/1988 | Monticelli ................................. 606/56 |
| 4,923,458 | 5/1990 | Fischer . |
| 5,095,919 | 3/1992 | Monticelli ................................. 606/56 |
| 5,405,347 | 4/1995 | Lee et al. . |
| 5,496,319 | 3/1996 | Allard et al. ............................. 606/56 |
| 5,662,650 | 9/1997 | Bailey et al. . |
| 5,797,908 | 8/1998 | Meyers ..................................... 606/56 |

FOREIGN PATENT DOCUMENTS

| | | |
|---|---|---|
| WO 97/30650 | 8/1997 | WIPO . |
| WO 97/30651 | 8/1997 | WIPO . |

OTHER PUBLICATIONS

Synthes brochure entitled "The AO/ASIF Hybrid Fixator Technique Guide", 13 pgs., undated.
Zimmer brochure entitled "Hybrid Application", 6 pgs., undated.
Brochure entitled "Monticelli Spinelli External Fixation System", 2 pgs., undated.
Ace brochure entitled "Wire Tension Treatment of Complex Tibial Plateau & Pilon Fractures", 4 pgs., undated.
Orthofix brochure entitled "The Orthofix Periarticular Module", 7 pgs. undated.

*Primary Examiner*—Guy V. Tucker
*Attorney, Agent, or Firm*—Harness, Dickey & Pierce, P.L.C.

[57] ABSTRACT

An external fixator for adjustably securing first and second portions of a bone includes a ring assembly and a bone screw clamp assembly interconnected by a central body. The ring assembly secures one or more tension wires adapted to pass through the first portion of the bone. The bone screw clamp assembly secures one or more bone screws adapted to engage a second portion of the bone. The ring assembly includes a generally circular frame having a peripheral groove for securing a tension wire carriage anywhere therealong. The tension wire carriages are adjustable so that the tension wire may be positioned above or below the ring. One or more connector rods are used to rigidify the external fixator by interconnecting the ring assembly and the bone screw clamp assembly.

21 Claims, 5 Drawing Sheets

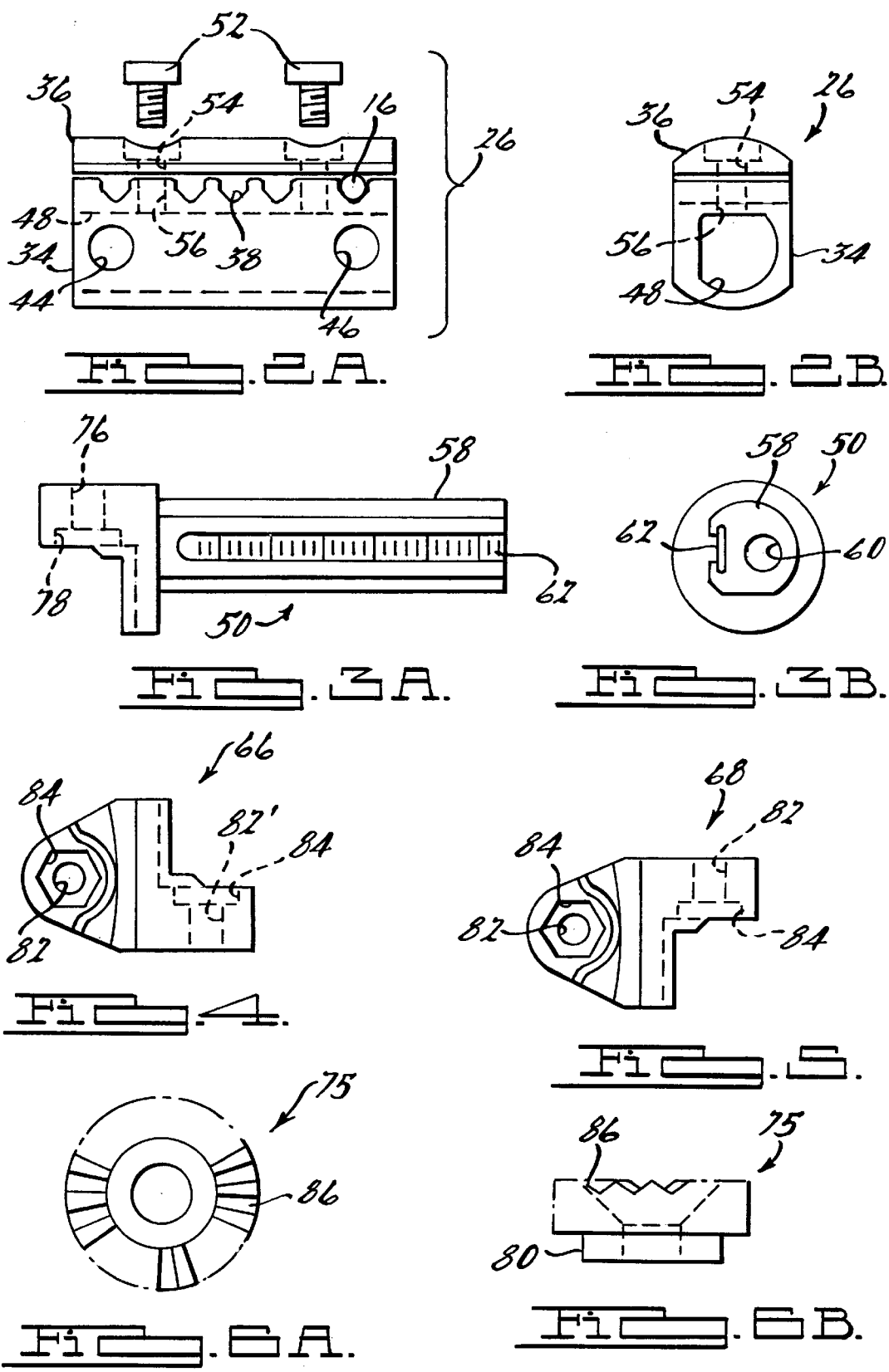

RING SYSTEM FOR EXTERNAL FIXATION OF BONE AND RELATED METHOD

BACKGROUND OF THE INVENTION

1. Field of the Invention

The present invention relates generally to an external fixator for use in orthopedic surgical applications. More particularly, the present invention relates to a ring system for external fixation of bone and a related method.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed in their desired positions during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first pair of bone screws to the apparatus while permitting the first pair of bone screws to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is known to employ a ring assembly which encircles a bone and is securely attached thereto with tension wires. For example, U.S. Pat. No. 4,784,125 to Monticelli, et al. discloses an external fixation system incorporating a pair of rings adapted for independent securement to a bone. The external fixation system contains a plurality of threaded rods connecting the two rings, thereby providing flexibility in inserting bone screws and an ability to distract the bone.

While known external fixation systems incorporating rings for surrounding a bone have proven to be suitable for certain applications, they are all associated with disadvantages. In this regard, known external fixation systems of the type shown in U.S. Pat. No. 4,784,125 require independent rotation of multiple threaded connecting rods to facilitate bone distraction. In addition, known ring systems for external fixation typically allow for wire fixation only at fixed points above or below one of the rings. The optimal location to secure a wire may not be at one of these fixed points and it may be difficult to offset the ring from the joint space.

SUMMARY OF THE PRESENT INVENTION

The present invention provides a ring system for external fixation of bone which allows for flexibility in engaging the bone with bone screws and tension wires. The tension wires are interconnected to a ring assembly through wire carriages. Tension wires are beneficial in certain surgical applications. For example, some fractures are too damaged for a conventional bone screw. These types of fractures can now be stabilized with the ring system of the present invention.

The ring system of the present invention incorporates carbon fiber connector rods which are secured to the ring assembly through a connector rod carriage. The connector rods are then attached to a bone screw through a supplemental base clamp. The resulting triangular structure increases the strength of the overall system. Carbon fiber is a radiographic translucent material so the utilization of the connector rods does not effect the radiographic viewing of the bone.

The ring assembly has an arcuate length with an outer grooved surface for receiving the wire carriages and connector rod carriages. Advantageously, the wire carriages and connector rod carriages can be located anywhere about the ring assembly to eliminate any restrictions on tension wire or connector rod placement circumferentially about the ring assembly. The wire carriages permit the tension wires to be adjustably located above or below the ring assembly. This allows the ring assembly to be moved away from a fracture line or a joint line for easier viewing. Since the wire carriages and connector rod carriages can be inserted into the groove anywhere around the ring assembly, a surgeon has significantly more options for the positioning of additional wires or bone screws. Once a carriage is inserted into the groove, the carriage can be properly positioned. Once properly positioned, a locking bolt is tightened to secure the selected position.

In one form, the present provides an apparatus for the external fixation of a bone. The apparatus includes a tension wire adapted to retain a first bone portion. The external fixation device further includes a clamping member for receiving the tension wire and a frame having a generally arcuate length. The frame includes a groove adapted to receive a portion of the clamping member in any desired position along the length. The groove opens in a direction substantially perpendicular to the bone.

An advantage of the present invention is the provision of a method and apparatus for external fixation of bone which overcomes the above-discussed and other disadvantages associated with known external fixators.

A related advantage of the present invention is the provision of a method and apparatus for external fixation of bone which does not constrain wire positioning about a ring.

Another advantage of the present invention is the provision of a method and apparatus for external fixation of bone in which wire carriages clamp into a groove provided in an outer surface of an arcuate frame.

Another advantage of the present invention is the provision of a method and apparatus for external fixation of bone which allows for distraction of a ring assembly through operation of a single mechanism.

Another advantage of the present invention is the provision of a method and apparatus for external fixation of bone which incorporate carbon fiber connector rods for rigidifying a system incorporating a ring assembly.

Another object of the present invention is the provision of a method and apparatus for external fixation of bone which incorporates wire carriages permitting tension wires to be located within an adjustable range above and below the ring.

Another object of the present invention is the provision of a ring assembly which can be readily used with existing external fixation components.

BRIEF DESCRIPTION OF THE DRAWINGS

FIGS. 2(A)–(B) are illustrations showing the bone screw clamping assembly shown in FIG. 1 according to the teaching of the preferred embodiment of the present invention.

FIGS. 3(A)–(B) are illustrations of a rail member shown in FIG. 1 according to the teachings of the preferred embodiment of the present invention.

FIG. 4 is an illustration of a first rotational component shown in FIG. 1 according to the teachings of the preferred embodiment of the present invention.

FIG. 5 is an illustration of a second rotational component shown in FIG. 1 according to the teachings of the preferred embodiment of the present invention.

FIGS. 6(A)–(B) are illustrations showing one of the grooved locking washers shown in FIG. 1 according to the teachings of the preferred embodiment of the present invention.

DETAILED DESCRIPTION OF THE PRESENT INVENTION

The following description of the preferred embodiment of the present invention is merely exemplary in nature and is in no way intended to limit the invention or its application or uses.

Figure 1:
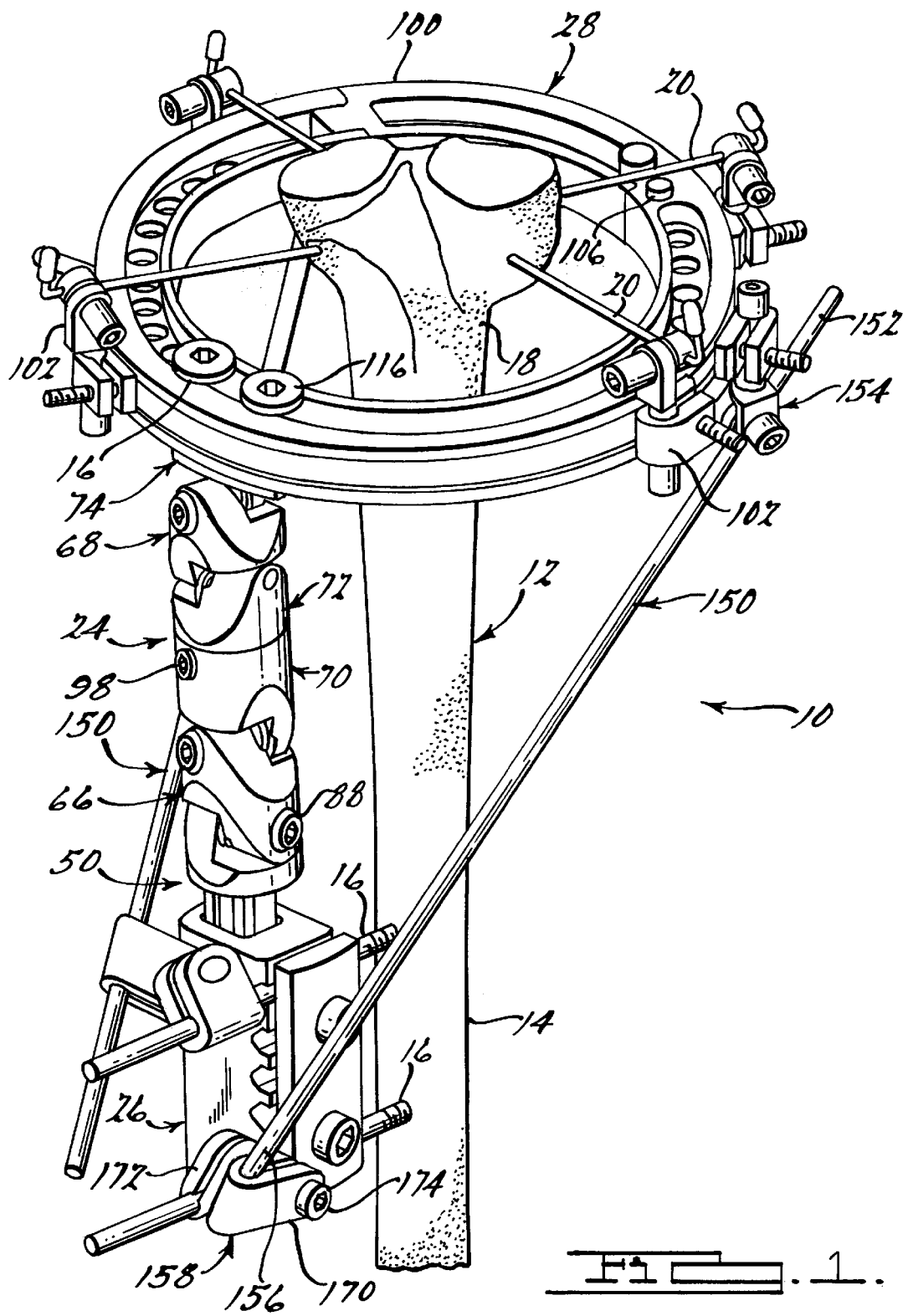
FIG. 1 is an elevational view of the apparatus for external fixation of bone according to the teachings of the preferred embodiment of the present invention shown in operative association with a bone.
Figure 7A:
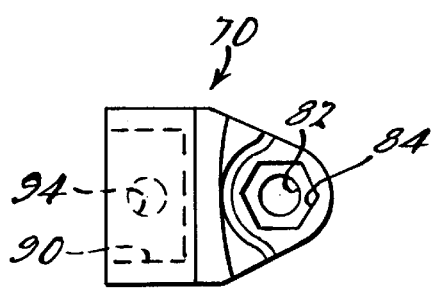
FIGS. 7(A)–(C) are illustrations of a first connector member shown in FIG. 1 according to the teachings of the preferred embodiment of the present invention.
Figure 7B:
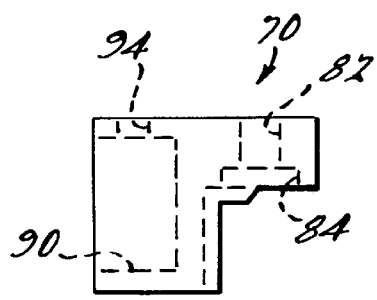
Figure 7C:
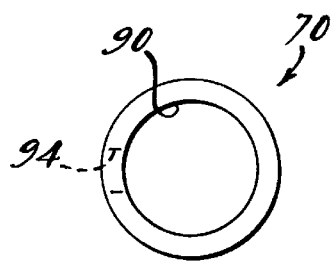
Figure 8A:
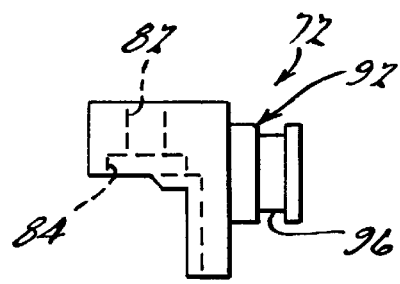
FIGS. 8(A)–(B) are illustrations of a second connection member shown in FIG. 1 according to the teachings of the preferred embodiment of the present invention.
Figure 8B:
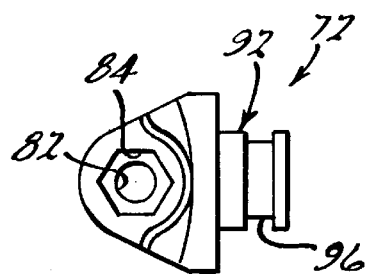
Figure 9A:
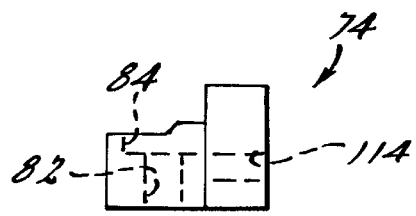
FIGS. 9(A)–(B) are illustrations of a ring adapter component shown in FIG. 1 according to the teachings of the preferred embodiment of the present invention.
Figure 9B:
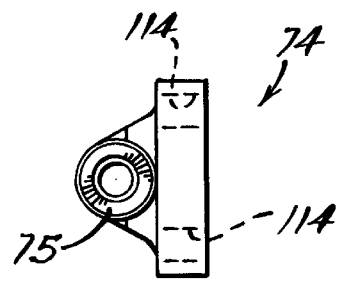

Referring to FIG. 1, an apparatus for external fixation of bone constructed in accordance with the teachings of a preferred embodiment of the present invention is generally identified at reference numeral 10. In the exemplary application illustrated, the apparatus 10 is shown operatively associated with a tibia 12. However, it will become readily apparent to those skilled in the art that the teachings of the present invention have applicability for the external fixation of a wide range of bones. The apparatus 10 is shown connected to a first portion or distal end 14 of the bone 12 through a pair of bone screws 16 and a second portion or proximal end 18 of the bone 12 through a pair of tension wires 20.

With continued reference to FIG. 1, the apparatus 10 is shown to generally comprise a central body 24 as well as a bone screw clamping assembly 26 and a ring assembly 28. The central body 24 is articulated to provide proper longitudinal rotational location of the bone screws 16 with respect to the ring assembly 28. The bone screw clamping assembly 26 is used to secure the bone screws 16 to the central body 24 while permitting the bone screws 16 to be axially displaced from the central body 24. The ring assembly 28 is able to interconnect the tension wires 20 to the central body 24.

The principal focus of the present invention relates to the construction and operation of the ring assembly 28, as well as the interconnection of the ring assembly 28 to the bone 12, the central body 24 and the bone screw clamping assembly 26. In this regard, it will be understood that the central body 24 and the bone screw clamping assembly 26 may be of any suitable configuration for interconnection of the bone screws 16 with the ring assembly 28. It will be understood that the ring assembly 28 may be readily incorporated into a system of external fixation components including elements which may alternatively be used in other applications. For purposes of fully describing the exemplary embodiment illustrated throughout the drawings, the ring assembly 28, as well as the bone screw clamping assembly 26 and the central body 24, will be described fully below.

The bone screw clamping assembly 26 will be described in greater detail with reference to FIGS. 2(A)–2(B). The bone screw clamping assembly 26 includes a base portion 34 and a cover portion 36. The base portion 34 preferably serves to receive the pair of bone screws 16 in two of a plurality of grooves 38, while the cover portion 36 serves to secure the bone screws 16 within the grooves 38. The grooves 38 are preferably illustrated to include two contact surfaces which are substantially planar so as to permit line contact of the bone screws 16 in two positions within the grooves 38. Since the bone screws 16 also engage the cover portion 36 of the bone screw clamping assembly 26, the bone screws 16 engage the bone screw clamping assembly 26 in three positions (i.e., along the contact surfaces as well as on the cover portion 36). This provides line contact which secures the bone screws 16 in a more effective manner than if the grooves 38 were cylindrical.

The base portion 34 of the bone screw clamping assembly 26 further includes a first aperture 44 and a second aperture 46. The first aperture 44 is used to receive a threaded member (not shown) which is able to secure a compression/distraction member (not shown) within a D-shaped central bore 48 of the bone screw clamping assembly 26. One suitable compression/distraction member is shown and described in commonly assigned U.S. Pat. No. 5,662,650. The second aperture 46 is used to receive a threaded member (not shown) which serves to secure a rail member 50 in a locked position as will be more fully discussed below.

The cover portion 36 of the bone screw clamping 26 is secured to the base portion 34 by means of two screws 52. To accommodate these screws 52, the cover portion 36 of the bone screw clamping assembly 26 includes two apertures 54 (shown in phantom in FIGS. 2(A) and 2(B)) which mate with corresponding apertures 56 in the base portion 34 of the bone screw clamp 26. Accordingly, upon secured threaded engagement of the screws 52 within the apertures 54 and 56, the cover portion 36 of the bone screw clamp 26 may be secured to the base portion 34 of the bone screw clamp 26.

To provide means for laterally displacing the bone screw clamp 26 with respect to the central body 24, the bone screw clamping assembly 26 further includes the rail member 50. The rail member 50, which is illustrated most clearly in FIGS. 3A–3B, includes a D-shaped extension 58 which is received in the D-shaped bore 48 of the bone screw clamping assembly 26. Because of the cross-sectional shape of the D-shaped extension 58, the base portion 34 of the bone screw clamping assembly 26 is able to slide on the D-shaped extension 58 of the rail member 50, though the base portion 34 is unable to rotate with respect to the D-shaped extension 58. The compression/distraction member engages a threaded aperture 60 located in the D-shaped extension 58.

The rail member 50 further includes a groove 62 which is disposed on the surface of the D-shaped extension 58. The location of the groove 62 is such as to permit the groove 62 to be located adjacent to the aperture 46 when the D-shaped extension 58 of the rail member 50 is inserted into the D-shaped bore 48 of the base portion 34. As will be apparent to those skilled in the art, the threaded member can then be inserted into the aperture 44 of the base portion 34 of the bone screw clamping assembly 26 so as to securely engage the groove 62 of the D-shaped extension 58 thereby preventing axial movement of the base portion 34 with respect to the rail member 50. In the preferred embodiment, the groove 62 includes graduated markings indicating the amount of longitudinal displacement of the bone screw clamping assembly 26 relative to the central body 24.

The central body 24 will now be described in greater detail with reference to FIGS. 4–9B. The central body 24 is shown to generally include first and second connection members 66 and 68, first and second rotational components 70 and 72, and a ring adapter member 74.

A plurality of grooved locking washers 75 are disposed between various components of the central body 24. For example, the rail member 50 has an aperture 76 with a hex-shaped recess 78 for receiving a base portion 80 of the washer 75. In a similar fashion, the first connection member 66 includes a first aperture 82 with a hex-shaped recess 84 for receiving the base portion 80 of a washer 75. Because the washers 75 each include cooperating grooved surfaces 86 adapted to lockingly engage each other, the first connection member 66 is secured to the rail member 50 upon secured threaded engagement of a screw 88 (shown in FIG. 1) with internal threads of the aperture 76. The screw 88 defines a pivot axis between the first connection member 66 and the rail member 50. The joint permits approximately 60° of relative rotation. However, this range of relative rotation may be readily adjusted for particular applications. In a substantially identical manner, the first connection member 66 is attached to the first rotational component 70, the second rotational component 72 is attached to the second connection member 68, and the second connection member 68 is attached to the ring adapter member 74. Briefly, the first connection member includes a second aperture 82' including a hex-shaped recess 84. Additionally, the second connection member includes first and second apertures 82 and 82' with hex-shaped recesses 84 which are identical to those of the first connection member 66. Further, the first and second rotational components 70 and 72 and the ring adapter member 74 each include an aperture 82 having a recess 84 which is identical to that of the first connection member 66.

The first rotational component 70 is shown to include a cylindrical recess 90 adapted to receive a male extension 92 carried by the second rotational component 72. The cylindrical recess 90 and the cooperating male extension 92 permit relative rotation about an axis substantially parallel to the axis to the bone 12. The first rotational component 70 includes an aperture 94 which intersects the cylindrical recess 90 and is adapted to align with a reduced diameter portion 96 of the male extension 92. The aperture 94 is internally threaded and adapted to receive a threaded fastener 98 (shown in FIG. 1). Upon tightening of the threaded fastener 98, relative rotation between the first and second rotational component 70 and 72 is prevented.

Figure 12:
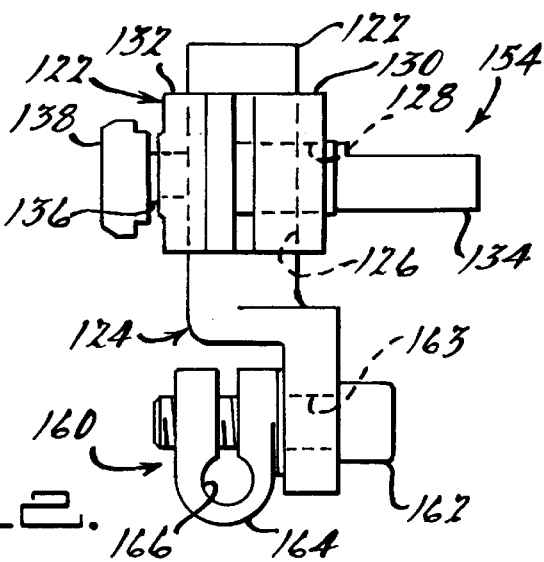
FIG. 12 is an illustration of one of the connector rod carriage assemblies of FIG. 1 according to the teachings of the preferred embodiment of the present invention.

With continued reference to FIG. 1 and additional reference to FIGS. 10–12, the ring assembly 28 of the preferred embodiment of the apparatus 10 of the present invention will now be described in detail. The ring assembly 28 is shown to generally include a ring or frame 100 having an arcuate length and a plurality of tension wire carriages 102. The ring 100 preferably includes a first arcuate member 103 and a second arcuate member 104 which cooperate to form a complete circle for surrounding the bone 12. In the embodiment illustrated, the first arcuate member 103 is approximately two thirds of a complete circle, while the second arcuate member 104 is approximately one third of a complete circle. As shown in the exemplary application of FIG. 1, the first and second arcuate members 103 and 104 are simultaneously used. However, it will be understood that either the first arcuate member 103 or the second arcuate member 104 may be employed by itself in situations in which a complete ring 100 is not necessary or would limit limb flexion or extension.

The first and second arcuate members 103 and 104 are connected to one another by bolts 106 (as shown in FIG. 1) which engage aligning apertures provided in cooperating ends. In this regard, each end of both of the first and second arcuate members 103 and 104 includes an extending tab 108 adapted to align with an internally threaded aperture of the opposite member 103 or 104. For example, the first arcuate member 103 includes a tab 108 having an aperture 109 which aligns with an internally threaded aperture 110 formed in an adjacent end of the second arcuate member 104.

Figure 10:
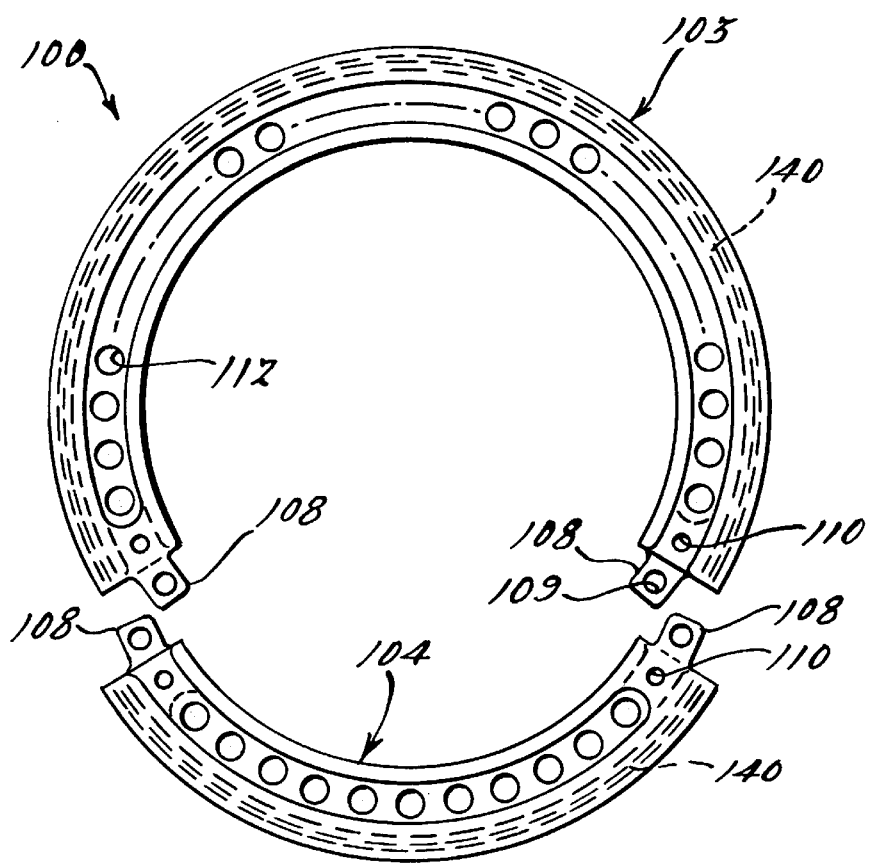
FIGS. 10 is an illustration of the ring assembly shown in FIG. 1 according to the teachings of the preferred embodiment of the present invention.
Figure 11:
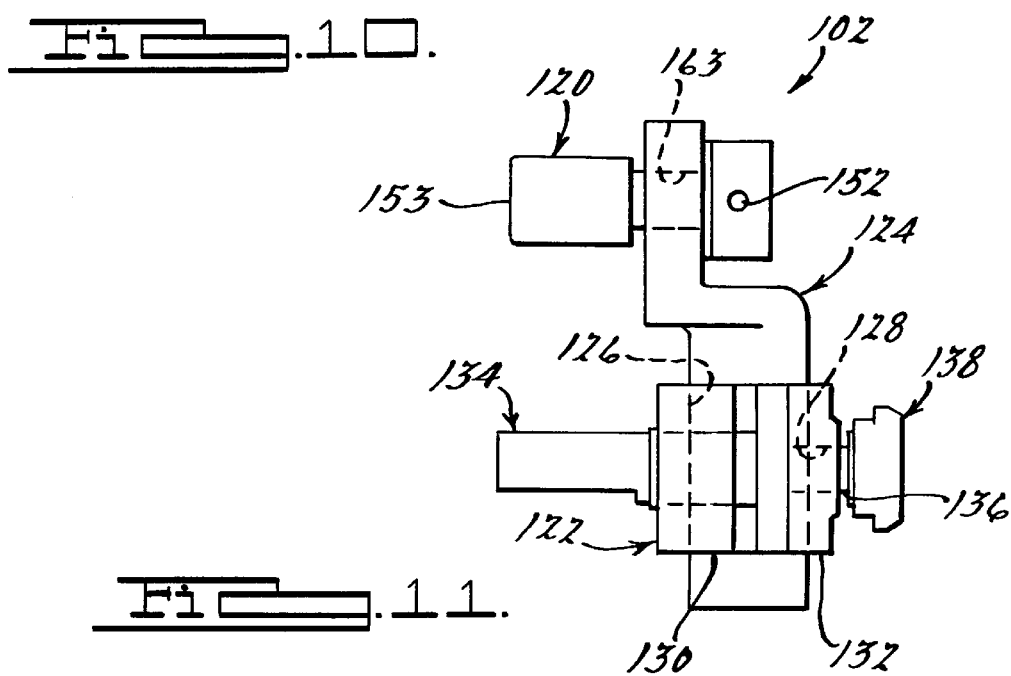
FIG. 11 is an illustration of one of the tension wire carriage assemblies of FIG. 1 according to the teachings of the preferred embodiment of the present invention.

As specifically shown in FIGS. 1 and 10, the ring or frame 100 includes apertures 112 formed about its circumference to facilitate attachment of the central body 24 to the ring assembly 28. The ring adaptor member 74 includes a pair of internally threaded apertures 114 adapted to align with a selected pair of apertures 112 of the ring 100. Threaded fasteners 116 (shown in FIG. 1) pass through the apertures 112 of the ring 100 and engage the internal threads of the apertures 114. In this manner, the central body 24 may be attached to the ring 100 at any point about its circumference.

The wire carriages 102, one of which is most clearly illustrated in FIGS. 11 and 13A–13C, function to securely interconnect the tension wires 20 and the ring 100. Each wire carriage 102 is illustrated to generally include a wire clamping portion 120 and a ring clamping portion 122 adjustably interconnected by an intermediate portion 124. The ring clamping portion 122 is generally U-shaped and has a vertically aligned aperture 126 for slidably receiving the intermediate portion 124. The ring clamping portion 122 further includes a horizontally aligned aperture 128 which passes through each of a pair of legs 130 and 132. The horizontally extending aperture 128 receives a threaded rod or locking bolt 134 which is rotatably engaged at a first end 136 with a clamping element 138.

The clamping element 138 is adapted to be received within a groove 140 formed in an outer face of the ring 100 about the entire circumference of the ring 100. The groove 140 is shown to preferably open in a direction substantially perpendicular to the bone 12. The ring 100 is further formed to include a first clamping flange 142 downwardly extending from an upper surface 143 and a second clamping flange 144 upwardly extending from a lower surface 146.

Figure 13A:
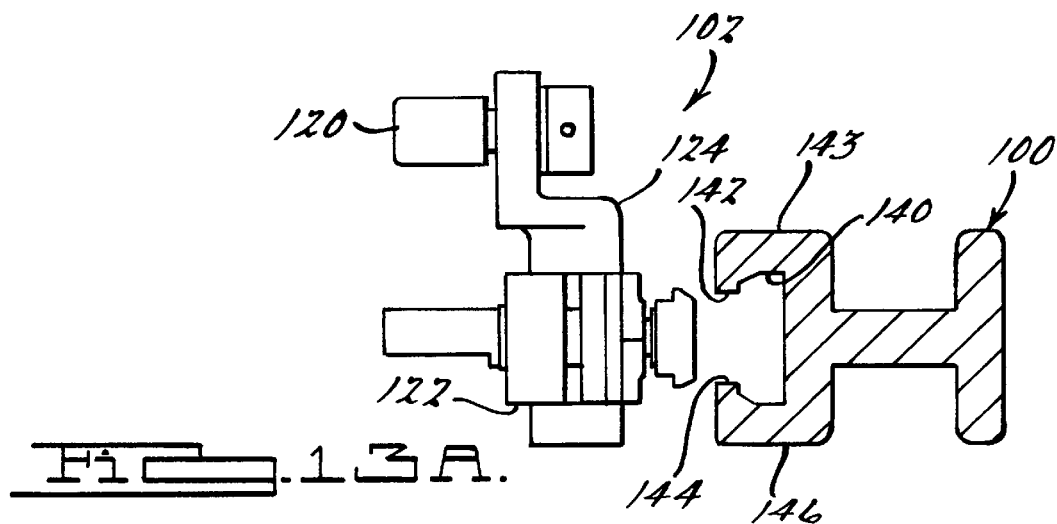
FIGS. 13(A)–(C) represent a series of cross-sectional views illustrating attachment of the tension wire carriage assembly of FIG. 11 to the ring assembly of FIG. 10.
Figure 13B:
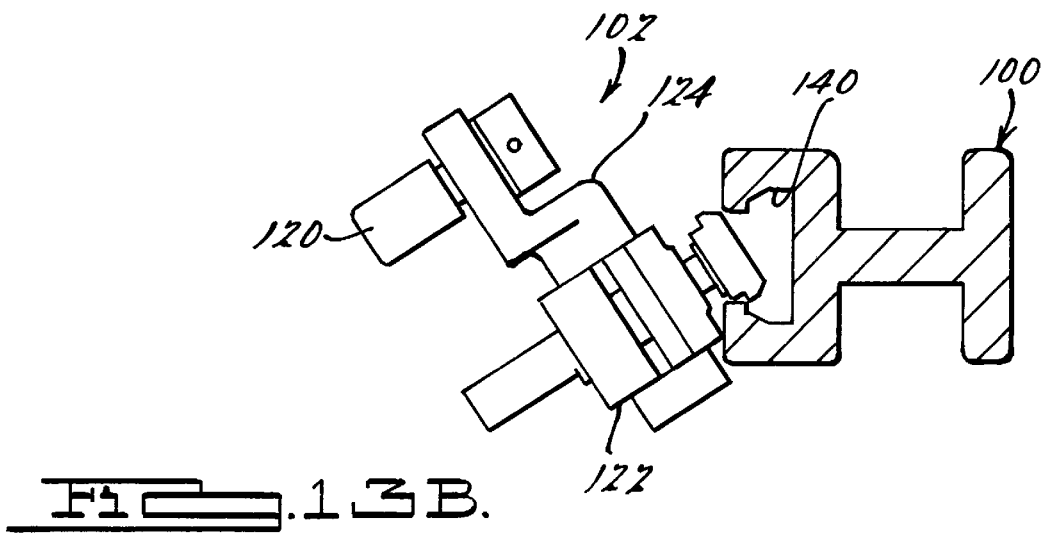
Figure 13C:
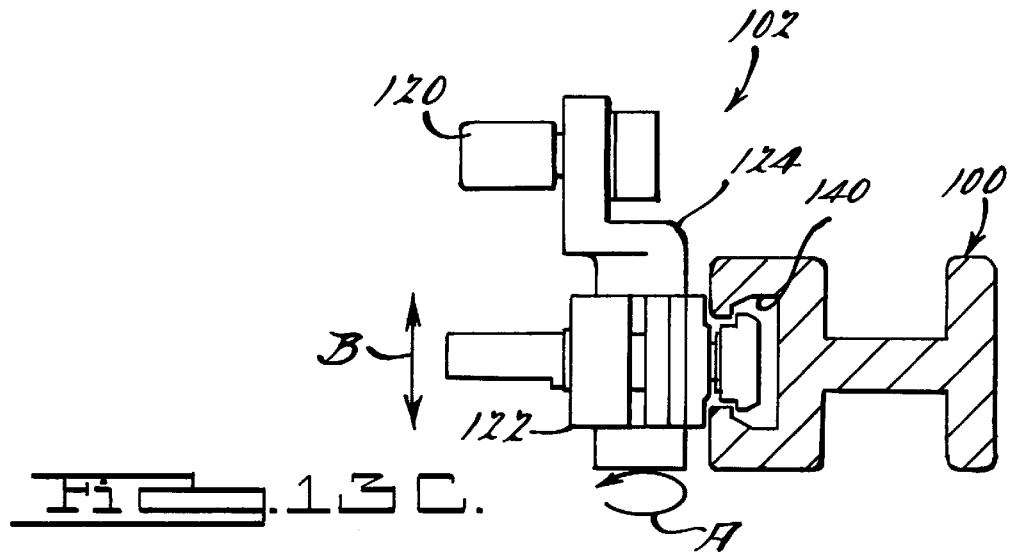

As shown specifically in FIGS. 13A–13C, when the threaded rod 134 is loosened within the horizontally aligned aperture 128, the wire carriage 102 can be angled so that a lower edge of the clamping member 138 may be inserted past one of the clamping flanges (for example the lower clamping flange 144). The wire carriage 102 is subsequently rotated so that an upper edge of the clamping element 138 may clear the other clamping flange (e.g. the first clamping flange 142). Upon tightening of the threaded rod 134, the first and second clamping flanges 142 and 144 are captured between the U-shaped clamp 122 and the clamping element 138.

The wire clamping portion 120 passes through a horizontally extending aperture 163 provided in an upper end of the intermediate portion 124. The wire clamping portion 120 is substantially conventional in construction and includes an aperture 152 for receiving the tension wire 20 and a rotatable lug 153 for clamping the tension wire 20 thereto. One suitable wire clamping portion is shown and described in PCT Application No. PCT/EP96/05652, which is hereby incorporated by reference.

The intermediate portion 124 of the wire carriage 20 provides a degree of adjustability of the tension wires 20 with respect to the ring 100. In this regard, the intermediate portion 124 may be rotated relative to the ring clamping portion 122 in a direction indicated by arrow A (shown in FIG. 13C) prior to tightening of the threaded rod 134. In addition, the intermediate portion 124 may also be linearly translated in the directions indicated by bi-directional arrow B.

As shown in the exemplary application of FIG. 1, the wire carriages 102 are oriented such that the tension wires 20 extend above the ring 100. Alternatively, it will be appreciated that the wire carriages 102 can be oriented such that the tension wires 20 extend below the ring 100. In one application, the wire carriages 102 permit the tension wires 20 to be located within a range approximately 2.5 cm above to approximately 2.5 cm below the ring 100. This allows the ring 100 to be moved away from a fracture line or a joint line so that easier viewing thereof is permitted.

As shown in the exemplary use application of FIG. 1, the ring assembly 28 is further interconnected to the screw clamping assembly 26 through a pair of connector rods 150. A first end 152 of each connector rod 150 is secured to the ring 100 through a connector rod carriage 154. A second end 156 of each connector rod 150 is secured to one of the bone screws 16 through a supplemental base clamp 158. As specifically shown in FIG. 12, the connector rod carriage 154 includes a ring clamping portion 122 and an intermediate portion 124 substantially identical to that of the wire carriage 102. For this reason, similar reference numerals have been used.

Rather than a wire clamping portion 120, the connector rod carriage 154 includes a rod clamping portion 160 which includes a fastener 162 which passes through an aperture 163 provided in the intermediate portion 124 and engages the legs of a U-shaped clamp 164. The U-shaped clamp 164 has an aperture 166 for receiving the connector rod 150. Alternatively, it will be appreciated that in certain applications the U-shaped clamp 164 may be utilized to engage a bone screw 16. Until the threaded fastener 162 is tightened, the connector rod 150 may slide within the aperture 166 and the U-shaped clamp 164 may rotate relative to the intermediate portion 124 about an axis defined by the fastener 162. While not shown, in certain applications it may be desired to interdispose serrations or locking washers between the intermediate portion 124 and the U-shaped clamp 164 for positive location therebetween.

As shown in FIG. 1, the supplemental base clamp 158 includes first and second U-shaped clamping portions 170 and 172 defining apertures for receiving the connector rod 150 and one of the bone screws 16, respectively. While not shown in specific detail, it will be understood that the supplemental base clamp 158 includes a threaded fastener 174 which passes through apertures provided in the U-shaped clamping portions 170 and 172. Prior to tightening of the fastener 174, the connector rod 150 and bone screw 16 may slide relative to the first and second clamping portions 170 and 172 and the first and second clamping portions 170 and 172 may rotate relative to one another about an axis defined by the fastener 174.

In the preferred embodiment, the connector rods 150 are constructed from a carbon fiber material. The triangular configuration incorporated by the connector rods 150 functions to increase the strength of the overall apparatus 10. The carbon fiber material of the connector rods 150 is a radiographic translucent material so that the utilization of the connector rods 150 does not adversely effect radiographic viewing of the bone 12.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for external fixation of a bone, the apparatus comprising:

a pin or wire adapted to engage a first portion of the bone;

a frame having a generally arcuate length and including a groove extending therealong, said groove being formed in an outer circumferential surface of said frame; and a carriage for interconnecting said pin or wire and said frame, said carriage having a first clamping portion for clamping said carriage in any desired position along said length of said frame, said first clamping portion including a clamping member insertable into said groove;

said frame including an upper surface and a lower surface, said groove located between said upper and lower surface;

said frame including first and second clamping flanges, each of said clamping flanges oriented substantially perpendicular to said upper and lower surfaces, said carriage adapted to releasably clamp at least one of said first and second clamping flanges.

2. The apparatus for external fixation of a bone of claim 1, wherein said carriages include a second clamping portion engaging said pin or wire, said second clamping portion being adjustable relative to said frame clamping portion along and about an axis substantially perpendicular to said upper and lower surfaces.

3. The apparatus for external fixation of a bone of claim 1, further comprising:

a pair of bone screws adapted to engage a second portion of the bone;

a bone screw clamping assembly for receiving said pair of bone screws; and an adjustable central body interconnecting said frame and said bone screw clamping assembly.

4. The apparatus for external fixation of a bone of claim 3, further comprising a connector rod interconnecting said frame and said bone screw clamping assembly.

5. The apparatus for external fixation of a bone of claim 4, further comprising a base clamp including a first portion clamping said connector rod and a second portion clamping one of said pair of bone screws.

6. An apparatus for external fixation of a bone, the apparatus comprising:

a tension wire adapted to retain a first portion of the bone;

a pair of tension wire carriages for receiving said tension wire; and a frame having a continuous and generally arcuate length adapted to circumferentially surround said first portion of the bone, said frame including an upper surface and a lower surface, said frame having a continuous transverse cross section including a groove located between said upper and lower surfaces and first and second clamping flanges, each of said clamping flanges oriented substantially perpendicular to said upper and lower surfaces, said carriage adapted to releasably clamp at least one of said first and second clamping flanges, said groove adapted to receive each of said tension wire carriages in any desired position along said length.

7. The apparatus for external fixation of a bone of claim 6, wherein each said tension wire carriage includes a tension wire clamping portion engaging said tension wire, said tension wire clamping portion being adjustable relative to said frame along and about a line perpendicular to said first and second surfaces.

8. The apparatus for external fixation of a bone of claim 6, further comprising:

a pair of bone screws adapted to engage a second portion of the bone;

a bone screw clamping assembly for receiving said pair of bone screws; and an adjustable central body interconnecting said frame and said bone screw clamping assembly.

9. The apparatus for external fixation of a bone of claim 8, further comprising a connector rod interconnecting said frame and said bone screw clamping assembly, and a base clamp including a first portion clamping said connector rod and a second portion clamping one of said bone screws.

10. The apparatus for external fixation of a bone of claim 8, further comprising means for distracting said frame relative to said bone screw clamping assembly.

11. An apparatus for external fixation of a bone, the apparatus comprising:

a tension wire adapted to retain a first portion of the bone;

first and second tension wire carriages for receiving first and second ends of said tension wire, respectively; and a frame having a continuous and generally arcuate length adapted to circumferentially surround said first portion of the bone, said frame having a transverse cross section including a groove and first and second continuous clamping flanges extending generally perpendicular to said length, said groove adapted to receive said first and second tension wire carriages in any desired position along said length;

a pair of bone screws adapted to engage a second portion of the bone;

a bone screw clamping assembly for receiving said pair of bone screws; and an adjustable central body interconnecting said frame and said bone screw clamping assembly.

12. The apparatus for external fixation of a bone of claim 11, wherein said frame includes an upper surface and a lower surface, said groove located between said upper and lower surfaces and opening in a direction substantially parallel to said length.

13. The apparatus for external fixation of a bone of claim 12, wherein said first clamping flange downwardly extends from said upper surface and said second clamping flange upwardly extends from said lower surface.

14. The apparatus for external fixation of a bone of claim 11, wherein each said tension wire carriage includes a tension wire clamping portion adjustably interconnected to said frame for translation along and rotation about a line substantially perpendicular to said length.

15. The apparatus for external fixation of a bone of claim 11, further comprising a connector rod interconnecting said frame and said bone screw clamping assembly, and a base clamp including a first portion clamping said connector rod and a second portion clamping one of said bone screws.

16. The apparatus for external fixation of a bone of claim 11, further comprising means for distracting said frame relative to said bone screw clamping assembly.

17. An apparatus for external fixation of a bone, the apparatus comprising:

a pin or wire adapted to engage the bone;

a frame including first and second spaced apart surfaces defining a groove, said first and second spaced apart surfaces being oriented generally parallel to one another, said frame including first and second clamping flanges, each of said clamping flanges oriented substantially perpendicular to said first and second spaced apart surfaces; and a carriage interconnecting said pin or wire and said frame, said carriage having a clamping portion including a clamping member insertable into said groove, said carriage adapted to releasably clamp at least one of said first and second clamping flanges.

18. The apparatus for external fixation of a bone of claim 17, wherein said frame includes a generally arcuate length and further wherein said groove extends substantially along said length.

19. The apparatus for external fixation of a bone of claim 18, wherein said groove is formed in an outer circumferential surface of said frame.

20. The apparatus for external fixation of a bone of claim 17, wherein said carriage includes a main body portion and a rotatable member threadably engaged with said main body portion, said rotatable member including an end coupled to said clamping member such that rotation of said rotatable member in a first direction draws said clamping member toward said main body portion.

21. The apparatus for external fixation of a bone of claim 20, wherein at least one of said first and second clamping flanges is clamped between said clamping member and said main body portion of said carriage.

* * * * *

UNITED STATES PATENT AND TRADEMARK OFFICE
CERTIFICATE OF CORRECTION

PATENT NO.   : 5,997,537
DATED        : December 7, 1999
INVENTOR(S)  : Stephen B. Walulik It is certified that error appears in the above-identified patent and that said Letters Patent is hereby corrected as shown below:

Column 1,
Line 24, delete 2nd occurrence of "a".

Column 2,
Line 6, delete "effect and substitute -- affect -- therefor.
Line 25, after "present" insert -- invention --.

Column 3,
Line 28, "FIGS." should be -- FIG --.

Column 5,
Line 49, after "clamping" insert -- assembly --.

Column 8,
Line 18, delete "effect" and substitute -- affect -- therefor.

Column 9, claim 8,
Line 29, change dependency to claim 8.

Signed and Sealed this

Ninth Day of April, 2002

Attest:

JAMES E. ROGAN
*Attesting Officer*  *Director of the United States Patent and Trademark Office*